US007370533B2

(12) United States Patent  (10) Patent No.: US 7,370,533 B2
Davis                      (45) Date of Patent:     May 13, 2008

(54) PORTABLE AUDIOMETER ENCLOSED WITHIN A PATIENT RESPONSE MECHANISM HOUSING

(75) Inventor: David M. Davis, Spring Mount, PA (US)

(73) Assignee: Otovation, LLC, King of Prussia, PA (US)

( * ) Notice: Subject to any disclaimer, the term of this patent is extended or adjusted under 35 U.S.C. 154(b) by 0 days.

(21) Appl. No.: 11/365,224

(22) Filed: Mar. 1, 2006

(65) Prior Publication Data
US 2007/0204694 A1 Sep. 6, 2007

(51) Int. Cl.
A61B 5/00 (2006.01)
H04R 29/00 (2006.01)

(52) U.S. Cl. ............................. 73/585; 381/60; 600/559
(58) Field of Classification Search .................. 73/585; 381/50, 314, 23.1; 600/559; 702/57
See application file for complete search history.

(56) References Cited

U.S. PATENT DOCUMENTS

| 3,536,835 | A  | * | 10/1970 | Rawls, Jr. et al. | 73/585 |
| 4,759,070 | A  | * | 7/1988  | Voroba et al. | 381/60 |
| 5,197,332 | A  | * | 3/1993  | Shennib | 73/585 |
| 5,428,998 | A  | * | 7/1995  | Downs | 73/585 |
| 6,350,243 | B1 | * | 2/2002  | Johnson | 600/559 |
| 6,366,863 | B1 | * | 4/2002  | Bye et al. | 702/57 |
| 6,468,224 | B1 | * | 10/2002 | Foreman et al. | 600/559 |
| 6,788,798 | B1 | * | 9/2004  | Backman | 381/372 |
| 6,964,642 | B2 | * | 11/2005 | Wasden et al. | 600/559 |
| 6,974,421 | B1 | * | 12/2005 | Causevic et al. | 600/561 |
| 7,016,504 | B1 | * | 3/2006  | Shennib | 381/60 |

* cited by examiner

Primary Examiner—Helen Kwok
(74) Attorney, Agent, or Firm—Woodcock Washburn LLP

(57) ABSTRACT

A portable audiometer for performing hearing testing enclosed within a patient response mechanism housing is disclosed. The audiometer may include a printed circuit board containing circuitry, plugs or other connectors for wired or wireless headphones and bone conductor, a battery charging unit, and one or more buttons for indicating response to pure tone and other stimuli, including, but not limited to noise, speech, and visual and audio instructions and graphical representations of objects or concepts used in a comprehensive hearing test. The instrument can be connected via a wired or wireless interface to a variety of controlling devices, including PC's, Personal Digital Assistants (PDA's), cellular phones, smartphones, including hybrid phone and PDA, and other devices such as media players, gaming systems, personal audio players, and other devices that can operatively communicate with the portable device.

19 Claims, 8 Drawing Sheets

PORTABLE AUDIOMETER ENCLOSED WITHIN A PATIENT RESPONSE MECHANISM HOUSING

FIELD OF THE INVENTION

The present invention relates to the field of portable audiometry used for hearing evaluation.

BACKGROUND OF THE INVENTION

Use of audiometers in the characterization of hearing patterns is well known in the art, and commonly used by audiologists, physicians, occupational health testers and industrial hygenists, school nurses and other testing personnel, audiologic technicians, and researchers, among others. Typical audiometers generate sine wave pure tones that are presented to the test subject and a response to the stimulus is given by verbal or hand signal, or via patient response mechanism such as a button that is externally connected via a cable or other similar means and is communicatively coupled to the audiometer. Both air conduction and bone conduction audiometry are widely practiced and employ different means of delivering the stimuli that help in localizing the source of hearing deficit in a subject. Specifications and calibrations of audiometers are well established and defined under a series of standards including both ISO and ANSI standards bodies.

Recent developments in linking computers to audiometers has resulted in a class of audiometers that are computer-driven, thereby enabling the storage of information and results more readily. These computer-operated audiometers create additional means to automate the testing process, and facilitate group as well as individual testing protocols.

Shennib (U.S. Pat. No. 5,197,332) teaches a design for implementing an audiometer within a headband used to also house the headphone transducers and other related peripherals necessary to embody a hearing aid testing system. This design offers some advantages in portability over more conventional audiometers, but requires a specific mounting and type of head gear to be worn, that limits the flexibility of types of audiometric transducers that can be used with the system without additional accessories or custom adaptations.

Since it may be desirable for an audiometer to include a patient control and response switch mechanism so that the patient can signal their acknowledgement of the stimuli, the inclusion of the audiometer into the response mechanism housing eliminates at least one extra component in a configuration, especially when automated testing is desired. This may make both the use and transportation of the audiometer more convenient, and address the portability as well as increasing reliability by reducing the number of components that must be used in the testing process.

SUMMARY OF THE INVENTION

The current invention provides a novel approach by embedding the audiometer within the housing of the mechanism that the patient uses to acknowledge the stimulus or provide other types of feedback consistent with a comprehensive hearing test, and does so in a way that optimizes both portability and flexibility of its use. The housing may be held by the test subject in their hand during the testing procedure, or it may be placed on a flat surface (such as a table top) convenient and comfortable for the test subject to access with their hand. In a variation of this embodiment of the invention, the housing may be suspended around the patient's neck via a lanyard or cord so that the housing rests against the chest of the subject, who may use their hand to signal response to the stimuli presented by, through, or in conjunction with the device.

The patient response mechanism may include one or a plurality of actuators such as buttons, switches, dials, biofeedback, or other means of signaling response to the presented stimuli, response to a visual cue, or manipulating parameters of the device, such as the frequency and intensity levels or moving from one stage of a test to another so as to enable the test subject to perform an automated test of various types and configurations. Additionally, a cover may be placed over or around the housing in order to make the device appear like something more friendly and/or familiar to the subject, such as a ladybug, racecar, or any of a variety of other appearances which may serve to make the presence of the device more comfortable and less intimidating for the test subject, which may be especially helpful when testing children.

Further, the use of the invention with a wireless communications method, such as Bluetooth, WiFi, wireless USB, and others that may be widely used, offers flexibility in positioning the test subject relative to the person administering or monitoring the test, and also facilitates testing of multiple test subjects concurrently. Additionally, in at least one embodiment, the tester and the subject may be at a distance from one another and still accomplish a complete and accurate audiometric testing process.

An advantage in the wireless mode of operation is the reduction in cables that link the subject to the tester, which can result in difficulties of entanglement and inadvertent changes in the quality of the connection via the cord with the attendant pulling or twisting that can occur as the subject may move during the testing process. The use of wireless headphones would provide further advantages in this scenario, by also eliminating the cord from the device to the headphones or earphones worn by the test subject.

The system may be operated with the test administrator and subject within a sound-proof enclosure, outside a sound-proof enclosure, or in a configuration of the test subject within and the test administrator outside the sound-proof enclosure.

As use of software can add to the flexibility of initiating, performing, tracking and generally controlling a testing protocol, and as there are a variety of microprocessor-based devices that run software and incorporate the necessary navigation, keyboard and/or screen functions to effect a testing method, it is highly desirable to create a system that can be used on a wide array of device types. Devices including PC's, Personal Digital Assistants (PDA's), smartphones (many of which include functions of both phone and PDA), and other devices such as media players, gaming systems, personal audio players, and other devices that can operatively communicate with the audiometer device represent flexibility for the test administrator to choose the device most convenient or readily available for administering a hearing test. It may also be desirable for software that runs on different types of devices to have a similar look and feel across the various types of screen sizes, resolutions, memory configurations and other characteristics that each may embody.

Finally, to achieve the flexibility of use to maximize the advantage of a portable audiometer housed within a patient response device, the invention may be operable under both DC and AC power.

Therefore, it may be desirable to implement an audiometer that has both the flexibility to use a variety of headphone, earphone, and bone conductor peripherals, provide an integrated patient response mechanism which has one or more actuators for patient response with an optional cover to make it friendlier for use by certain test subjects, and enable a wireless means to communicatively operate the audiometer from a variety of microprocessor-based devices.

BRIEF DESCRIPTION OF THE DRAWINGS

Other features of the present invention are further apparent from the following detailed description of the embodiments of the present invention taken in conjunction with the accompanying drawings, of which.

DETAILED DESCRIPTION OF ILLUSTRATIVE EMBODIMENTS

The invention provides electronics and other components in a portable enclosure that may include an integrated patient response mechanism, as well as connectors for the air conduction and optionally the bone conduction device, and communicate in a wired or wireless fashion to a microprocessor-based device that runs software to operatively communicate with the patient response device in order to manage or monitor a testing process in either a manual or automated fashion, as well as to transmit and receive audio signals for a variety of tests, such as speech testing and for instructions provided to the test subject. Such a portable enclosure may be, for example, a hand-holdable portable enclosure that is sized and shaped to fit comfortably in a single human hand.

Figure 1:
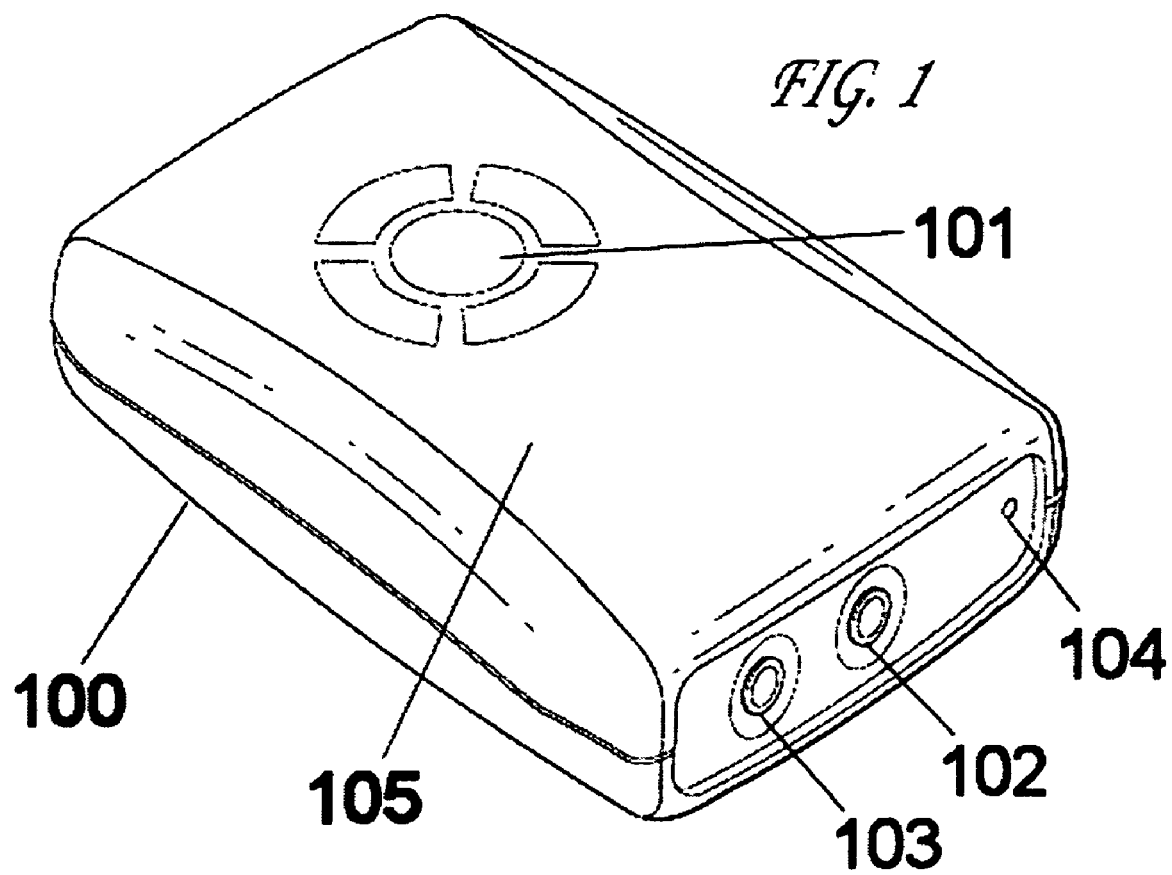
FIG. 1 depicts an example embodiment of the handheld device enclosure containing the audiometer.

The device housing (105) as shown in FIG. 1 may include an electronic assembly within the handheld unit that provides the circuitry and components of the audiometer. A battery compartment (not shown) may be removable for replacement of rechargeable or disposable batteries, or it may be sealed, depending on the type of battery used.

FIG. 1 shows an example embodiment of a handheld device (100) with patient response button(s) (101), and ports for connecting the headphone or earphone (102), bone conductor (103), and power supply/charger unit (104). The above configuration may be varied in order to accommodate a range of potential housing shapes and preferred operational formats without affecting the principal function of the device (100).

In an example embodiment of the patient response mechanism (101), a number of buttons or other types of actuators may be configured to represent the acknowledgement of the tone stimuli generated by the air or bone conductor, and also to denote other actions or respond to additional types of stimuli or information presented. These actions may be to enable navigation by the test subject within the test, such as from one frequency or tone intensity to another by means of pressing the buttons, or to acknowledge one of a number of choices presented. In an example configuration utilizing a plurality of buttons, the label of the button may be permanently marked on or near the button, or the labeling of the button may be context sensitive, that is, governed by the software and shown by an electronically controlled label so that various tests and configurations may be achieved by the same button depending on the test or step being administered by the system and operator.

It should be noted that while the following illustrations show right handed use, this configuration makes the device comfortable for both left and right handed use.

Figure 2:
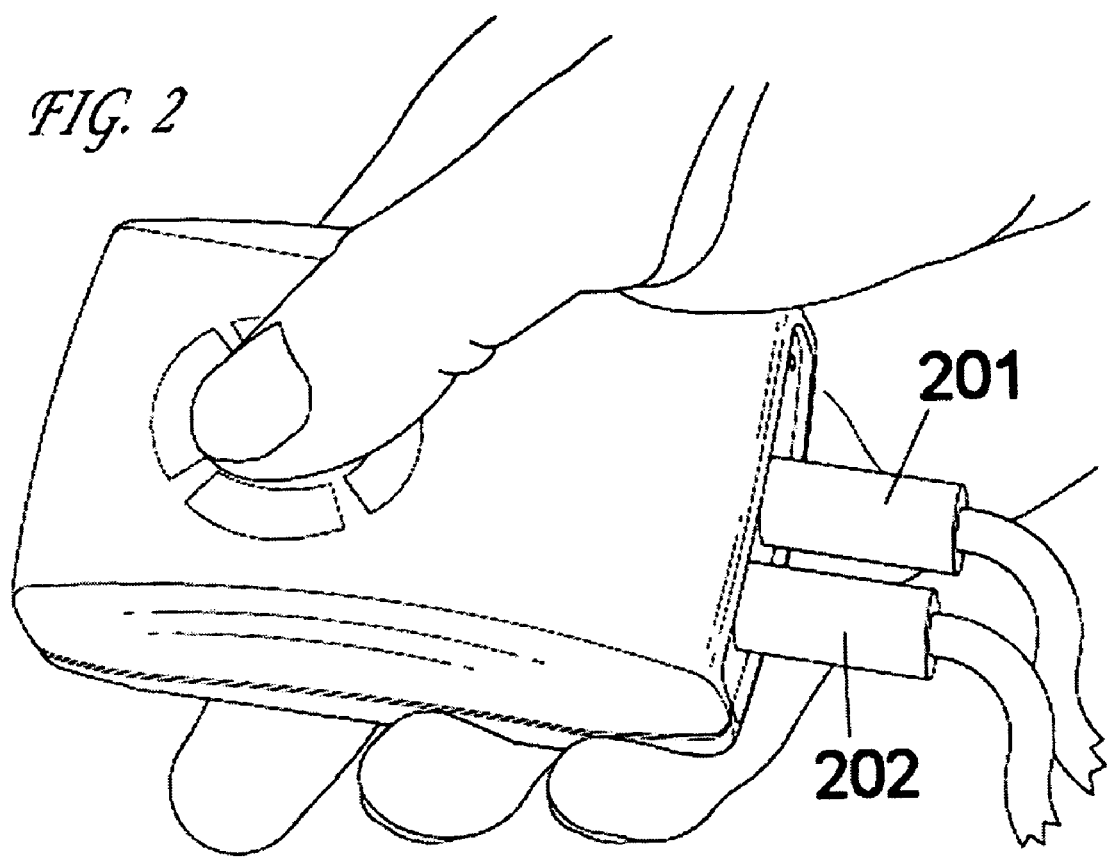
FIG. 2 shows the device embodiment held in hand and with the cords attached for air conduction headphones/earphones and bone conductor.

FIG. 2 depicts an example embodiment of a portable audiometer device held in the hand with the test subject's thumb being used to depress the response mechanism, and with the headphone or earphone cable (201) and optional bone conductor connection cable (202) shown connected to the end of the device.

In an example embodiment, the connectors used for the headphone and bone conductor cords may be a mini-DIN connector type, which provides for a secure and stable connection, avoiding the common problem of twisting that is well known in systems that use audio plugs, including, for example ¼" or ⅛" audio jacks. A collar-locking type of mini-DIN connector can be used that cannot be pulled out without lifting the collar first, thereby further reducing the possibility of the connection to the device being negatively affected unless the disconnection of the cord and the device is specifically intended.

Figure 3:
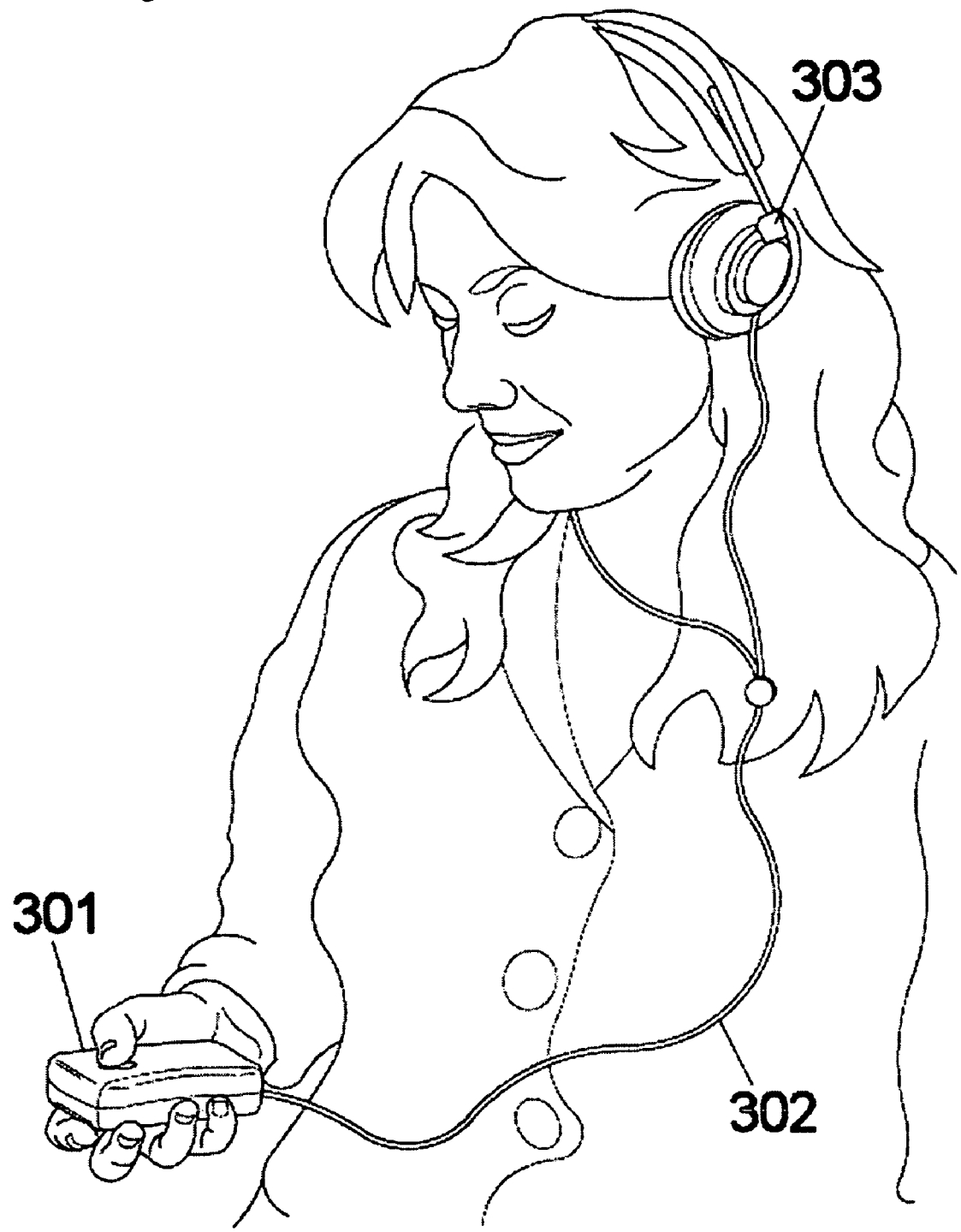
FIG. 3 depicts the typical configuration of use by a test subject.

FIG. 3 is an illustration of how a device according to the invention (301) may be held by a test subject, along with the cord connection to the headphones (302) and the headphones worn (303) to perform an air conduction hearing test. With the bone conductor connected, an additional cable and the bone conductor may be affixed to the mastoid bone behind the ear or forehead with the accompanying headband or other way of affixing the bone conductor to the intended area at the force required by governing standards.

Figure 4:
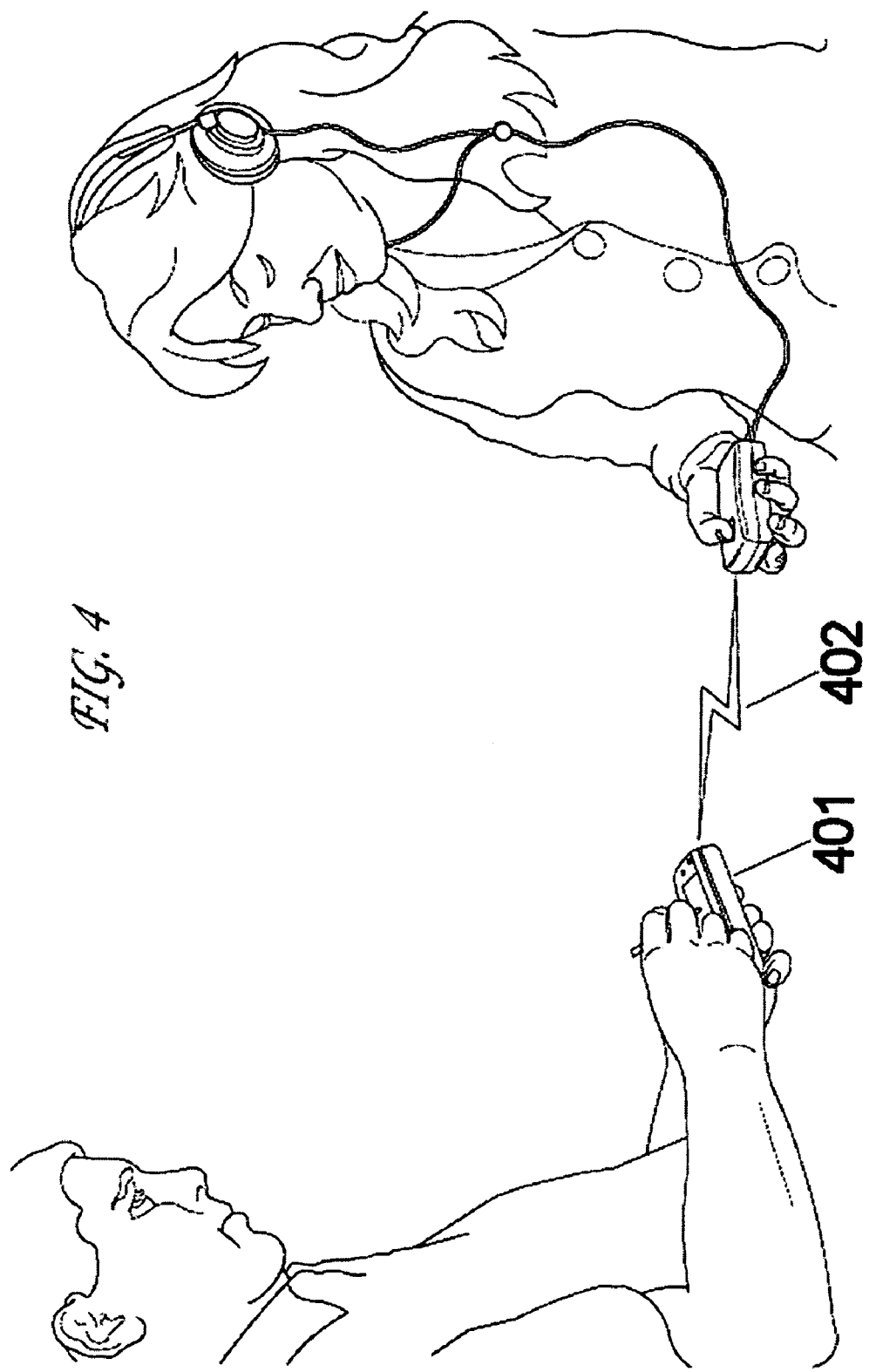
FIG. 4 illustrates one example of how a test subject and test operator may be oriented during a testing process.

FIG. 4 is an illustration of a testing configuration in which a person who is utilizing a microprocessor-based controlling device (401) can be positioned relative to and communicating wirelessly (402) with the a test subject operating the inventive device while taking a test. The microprocessor-based controlling device (401) may be any of a plurality of device types, including a personal computer ("PC"), personal digital assistant ("PDA"), phone, custom or hybrid device, media player, gaming system, personal audio player, or other device that can operatively communicate with the handheld audiometer.

Additionally, the controlling device (401) may transmit a series of test instructions to be stored in the device memory for automating the test procedure, so that it may be run independently by the test subject without intervention by the test administrator.

Figure 5:
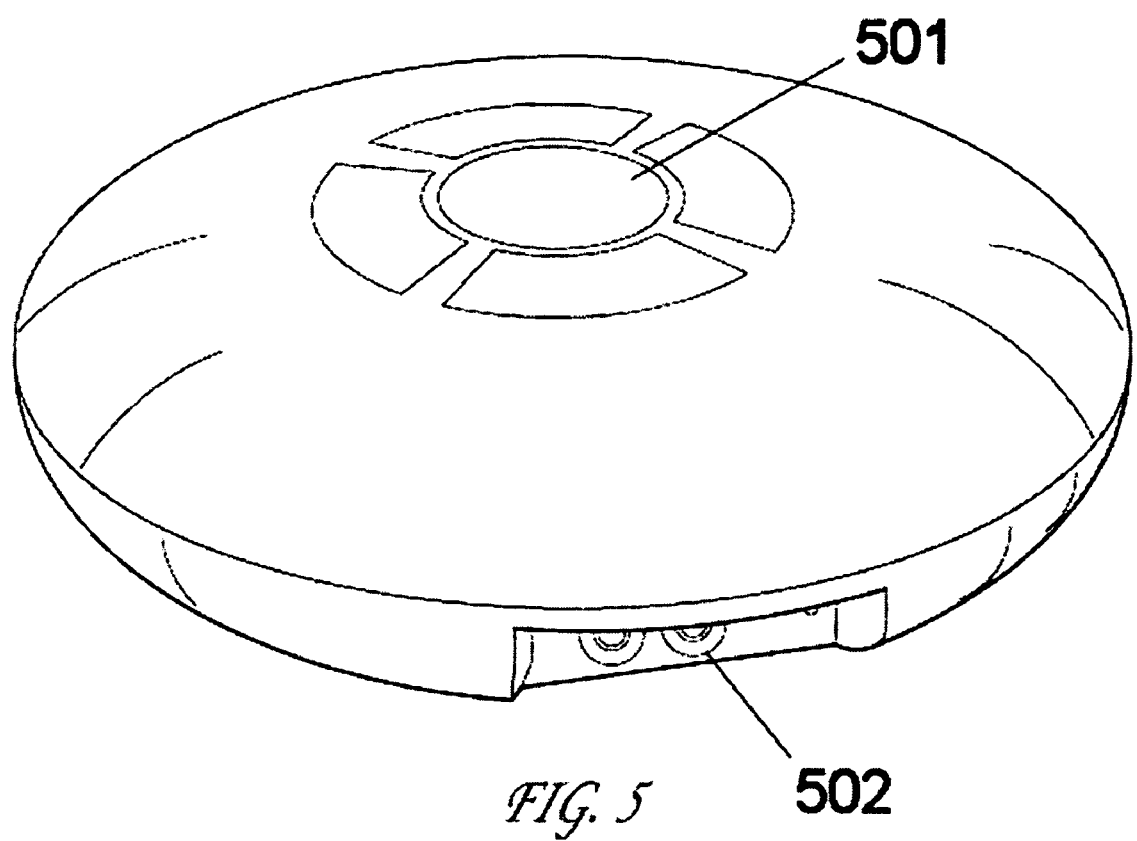
FIG. 5 is an alternate embodiment of the device as housed in a case suitable for table-top operation.
Figure 6:
FIG. 6 is an example of a test subject operating the alternate table-top embodiment.

FIG. 5 is an alternate embodiment of the device showing a housing that is suitable for use when positioned on a table or other flat surface, and enabling the user to operate the device in this position and orientation. In FIG. 5 as shown, the housing may have one or more patient response mechanisms (501) and plug and cord adapters (502). This configuration may be better suited than the configuration depicted in FIG. 1 to use in a setting where the test subject can be positioned to operate the unit on a table top or other comparable flat surface as shown in FIG. 6.

Figure 7:
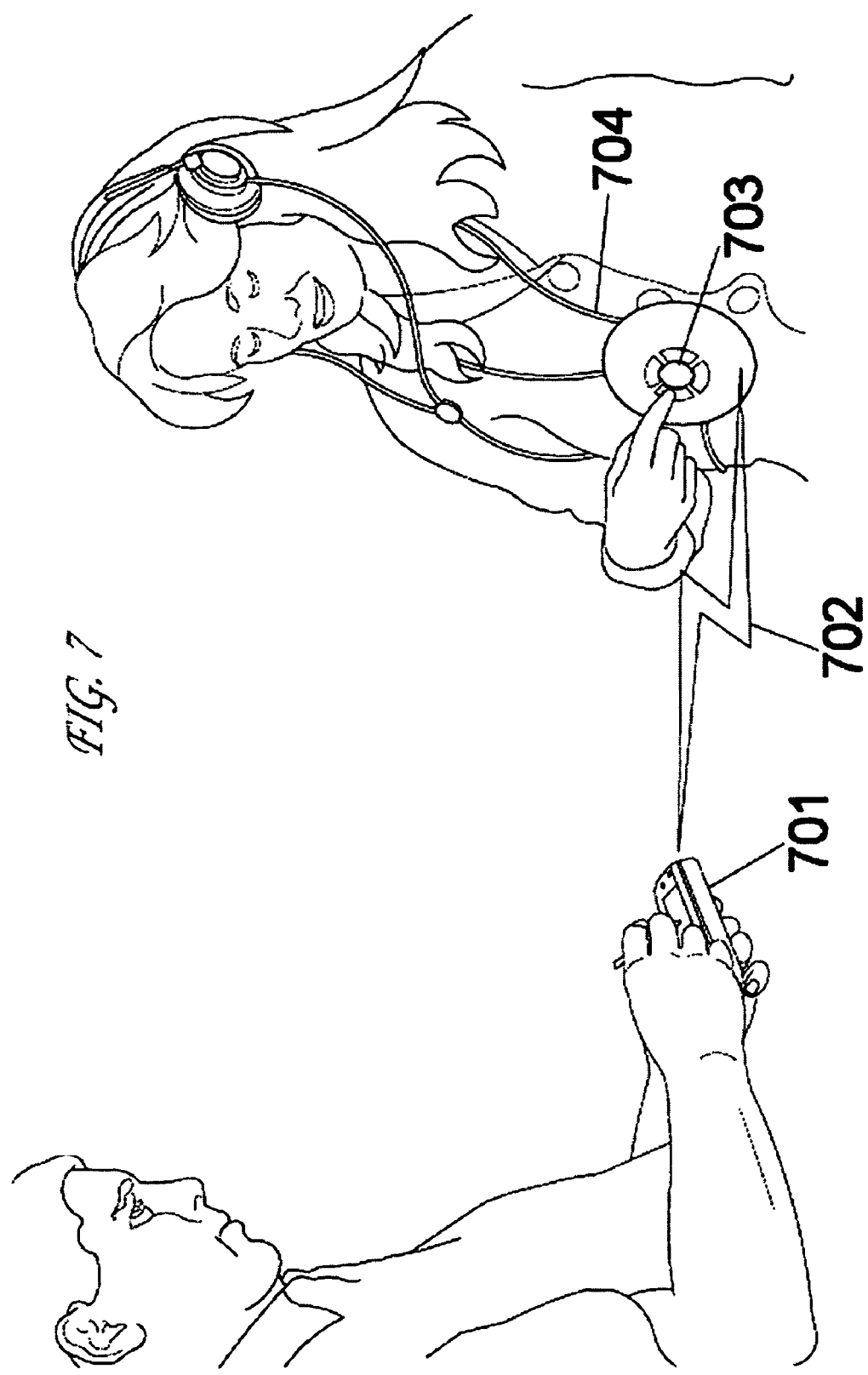
FIG. 7 depicts an alternate positioning of the embodiment as suspended around the neck of the test subject while the test process is performed.

FIG. 7 is an illustration of an alternative placement of the patient response mechanism enclosure as suspended from a cord (704) or other such means around the neck of the test subject for convenience and ease of use in various positions. The microprocessor-based controlling device (701) may be communicating wirelessly (702) with the audiometer, and the test subject may be able to use the patient response mechanism(s) (703) to acknowledge the stimuli or to respond to other visual or auditory information relating to the hearing test process. Note that the device embodiment depicted in FIGS. 1 through 4 may also be configured in this way, that is, suspended around the test subject's neck.

In another example embodiment, one or more test subjects may be located at a remote location to the test administrator, and the communications link of a direct remote connection or a networked environment such as the Internet may be used as the medium to connect the tester to one or multiple subjects while performing a testing process. In the event that an automated testing protocol is being administered, the testing protocol can be downloaded to the device's memory as a series of instructions that are defined by discrete characteristics that can be predetermined and defined by the test administrator, and the test can be run independently of the microprocessor-based controlling device.

Figure 8:
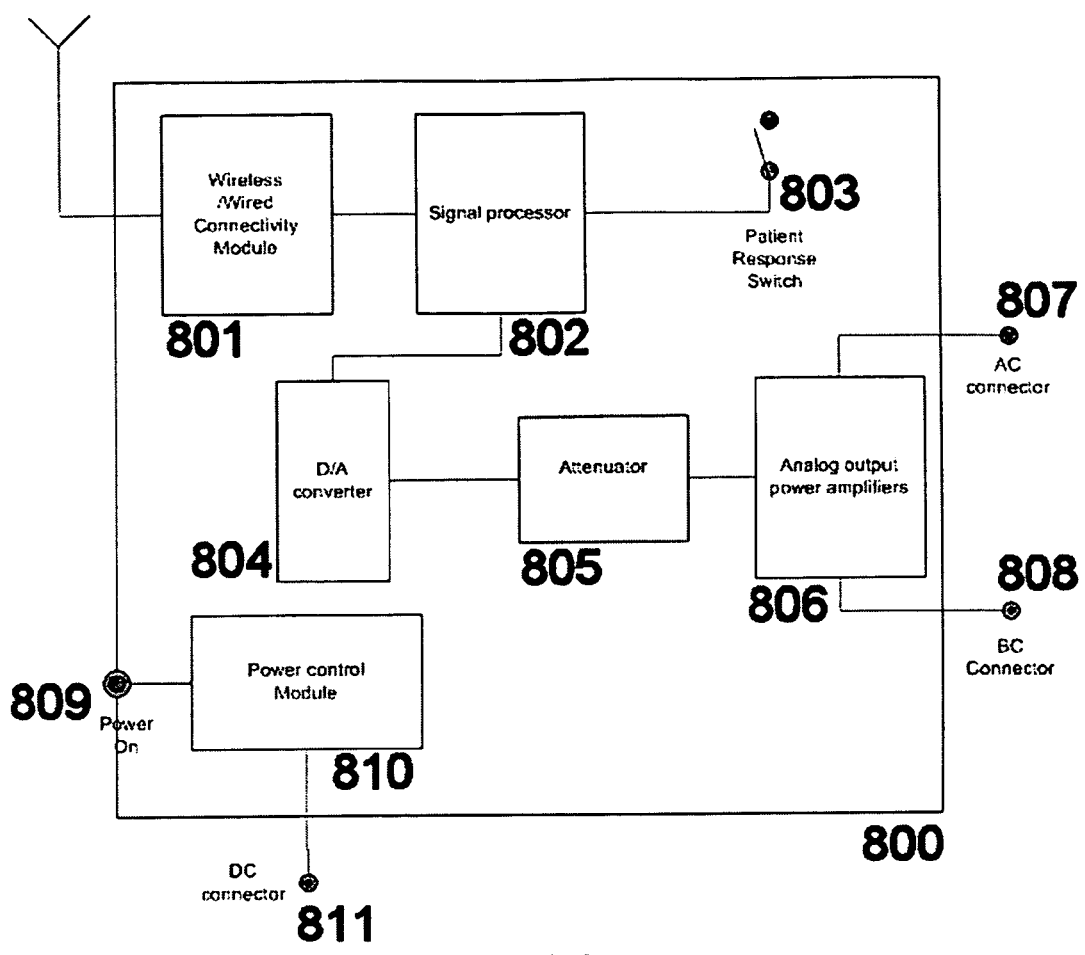
FIG. 8 is a block diagram that shows the essential components of the device circuitry.

FIG. 8 shows the block diagram that describes an example embodiment (800) of audiometer circuitry that may be contained within the device enclosure. A wireless/wired connectivity module (801) may be communicatively coupled with the controlling microprocessor-based device, which may pass commands to and from the signal processor (802) used to generate pure tone stimuli. The integral patient response mechanism (803) may handle the test subject interaction(s), and the D/A (digital-to-analog) convertor (804), attenuator (805), and analog output power amplifiers (806) may perform the necessary signal conditioning to then be output through either the air conduction headphone port (807) or the bone conductor via port (808). The power control module (810) may handle the AC and DC power management for the device, whose status may be managed by a switch/indicator (809) and a mains power DC connector (811).

Thus, a portable audiometer enclosed within a patient response mechanism housing has been described. Those skilled in the art will appreciate that numerous changes and modifications can be made to the preferred embodiments of the invention, and that such changes and modifications can be made without departing from the spirit of the invention.

What is claimed:

1. A portable audiometer device, comprising:
   a portable enclosure that is adapted for a user to hold in the user's hand, be worn around the user's neck, or be placed on a table-top remote from a microprocessor-based controlling or monitoring device;
   a patient response mechanism in said portable enclosure for signaling responses to sound stimuli;
   electronic audiometer circuitry in said portable enclosure that generates or delivers electrical signals representing the sound stimuli and records one or more patient responses;
   an acoustic transducer that is coupled to the audiometer circuitry for receiving the electrical signals and producing the sound stimuli; and
   a communications interface in said portable enclosure for wirelessly communicatively coupling the audiometer circuitry with said microprocessor-based controlling or monitoring device.

2. The audiometer device of claim 1, wherein the patient response mechanism includes at least one of a button, switch, dial, or other actuator.

3. The audiometer device of claim 1, wherein the patient response mechanism also enables navigation through or response to information presented during a testing process.

4. The audiometer device of claim 1, wherein the acoustic transducer also produces other aurally perceptible information.

5. The audiometer device of claim 1, wherein the transducer interface enables the acoustic transducer to be removably connected to the enclosure.

6. The audiometer device of claim 1, wherein the acoustic transducer includes an earphone.

7. The audiometer device of claim 1, wherein the acoustic transducer includes an insertion earphone.

8. The audiometer device of claim 1, wherein the acoustic transducer includes a bone vibrator.

9. The audiometer device of claim 1, further comprising a power supply port for connecting a power supply to the audiometer circuitry.

10. The audiometer device of claim 1, wherein the microprocessor-based device is at least one of a personal computer, a personal digital assistant, a phone, a custom or hybrid device, a media player, a gaming system, a personal audio player, or another device that can operatively communicate with the audiometer circuitry.

11. The audiometer device of claim 1, wherein the microprocessor-based device is adapted to manage, store, or retrieve data about a test subject or a test in such a way that an operation and general appearance of a respective user interface on each of a plurality of such microprocessor-based devices is similar in look, feel, and general operational form, independent of screen size, orientation, or other attributes that may differ from one such microprocessor-based device to another.

12. The audiometer device of claim 1, wherein the microprocessor-based device is adapted to monitor or control a plurality of tests performed simultaneously by a respective plurality of test subjects.

13. The audiometer device of claim 1, wherein the audiometer device comprises a patient-friendly cover over at least a portion of the portable enclosure or is otherwise made to resemble a patient-friendly object.

14. The audiometer device of claim 1, wherein the sound stimuli include at least one of tones, speech, or noise.

15. A portable audiometer device, comprising:
   a portable enclosure that is adapted for a user to hold in the user's hand, be worn around the user's neck, or be placed on a table-top remote from a microprocessor-based controlling or monitoring device;
   a patient response mechanism in said portable enclosure that enables navigation through or response to information presented during a testing process;
   electronic audiometer circuitry in said portable enclosure that generates or delivers electrical signals representing sound stimuli and records one or more patient responses;
   an acoustic transducer that is coupled to the audiometer circuitry for receiving the electrical signals and producing the sound stimuli; and a communications interface in said portable enclosure for wirelessly communicatively coupling the audiometer circuitry with said microprocessor-based controlling or monitoring device.

16. The audiometer device of claim 15, wherein the patient response mechanism includes at least one of a button, a switch, a dial, or another actuator.

17. The audiometer device of claim 15, where the patient response mechanism is labeled with an electronically-generated label that can be modified under software control during a test to provide context sensitivity to a type of stimulus, a location within a test process, or a response required to acknowledge the information presented.

18. The audiometer device of claim 15, where the information presented includes instructions or information relating to navigation through a testing procedure.

19. A method for testing hearing of a test subject, the method comprising:
providing the test subject with a portable audiometer system comprising:
a portable enclosure that is adapted for a user to hold in the user's hand, be worn around the user's neck, or be placed on a table-top remote from a microprocessor-based controlling or monitoring device,
a patient response mechanism in said portable enclosure that enables navigation through or response to information presented during a testing process,
electronic audiometer circuitry in said portable enclosure that generates or delivers electrical signals representing sound stimuli and records one or more patient responses,
an acoustic transducer that is coupled to the audiometer circuitry for receiving the electrical signals and producing the sound stimuli, and
a communications interface in said portable enclosure for wirelessly communicatively coupling the audiometer circuitry with said microprocessor-based controlling or monitoring device; and
enabling the test subject to respond to both the stimuli and information received via the communications interface and presented during the testing process, and to utilize the patient response mechanism to control a flow or sequence of the testing process in a self-directed manner.

* * * * *